United States Patent [19]
van Lake et al.

[11] Patent Number: 5,785,660
[45] Date of Patent: Jul. 28, 1998

[54] METHODS AND APPARATUS FOR STORING INTRACARDIAC ELECTROGRAMS

[75] Inventors: Paul van Lake, Scottsdale, Ariz.; David W. Adinolfi, Valencia, Calif.

[73] Assignee: Pacesetter, Inc., Sylmar, Calif.

[21] Appl. No.: 625,446

[22] Filed: Mar. 28, 1996

[51] Int. Cl.$^6$ ................................. A61N 1/362
[52] U.S. Cl. ............................ 600/523; 607/30
[58] Field of Search ................. 601/9, 16, 27, 601/30; 120/710, 697, 709; 600/510, 523, 522

[56] References Cited

U.S. PATENT DOCUMENTS

| | | |
|---|---|---|
| 3,782,367 | 1/1974 | Hochberg et al. . |
| 3,898,984 | 8/1975 | Mandel et al. . |
| 4,019,518 | 4/1977 | Maurer et al. . |
| 4,098,267 | 7/1978 | Stein et al. . |
| 4,142,533 | 3/1979 | Brownlee et al. . |
| 4,193,393 | 3/1980 | Schlager . |
| 4,281,664 | 8/1981 | Duggan . |
| 4,374,382 | 2/1983 | Markowitz . |
| 4,527,567 | 7/1985 | Fischler et al. . |
| 4,596,255 | 6/1986 | Snell et al. . |
| 4,625,730 | 12/1986 | Fountain et al. ............... 607/30 |
| 4,791,936 | 12/1988 | Snell et al. . |
| 4,809,697 | 3/1989 | Causey et al. . |
| 4,875,483 | 10/1989 | Vollmann et al. ............ 607/16 |
| 4,958,632 | 9/1990 | Duggan ........................ 607/30 |
| 5,012,411 | 4/1991 | Policastro et al. . |
| 5,139,028 | 8/1992 | Steinhaus et al. ............ 128/697 |
| 5,312,446 | 5/1994 | Holschbach et al. ......... 607/30 |
| 5,507,786 | 4/1996 | Morgan ........................ 607/27 |
| 5,513,645 | 5/1996 | Jacobson et al. ............. 607/27 |
| 5,518,001 | 5/1996 | Snell ........................... 128/697 |
| B1 4,019,518 | 10/1986 | Maurer et al. . |

Primary Examiner—William E. Kamm
Assistant Examiner—George R. Evanisko

[57] ABSTRACT

Methods and apparatus are provided for storing intracardiac electrogram (IEGM) and other cardiac data in an implantable cardiac device. When a physician wishes to create a cardiac data record containing the IEGM and other cardiac data, the physician directs the cardiac device to store the data on demand. A number of cardiac data records can be stored. Data records may also be stored after a delay period following a predetermined cardiac event. When the implantable cardiac device detects the predetermined cardiac event, the delay period begins. At the expiration of the delay period, the implantable cardiac device stores a cardiac data record. Cardiac data records can also be stored according to a predetermined schedule.

35 Claims, 2 Drawing Sheets

```
ARCHIVE SAMPLE.........#1....NSR @ 80 BPM
COUNTDOWN TIMER....................OFF
SENSE CONFIG......................BI RV SENSE
IEGM GAIN.........................10 MV / DIV
NSR @ 80 BPM  MAY 17, 1993      15:40:35
```

METHODS AND APPARATUS FOR STORING INTRACARDIAC ELECTROGRAMS

BACKGROUND OF THE INVENTION

This invention relates to methods and apparatus for storing intracardiac electrograms and other data, and more particularly, to methods and apparatus for selectively directing an implantable cardiac device to store records containing a patient's intracardiac electrogram and other cardiac sensor data on demand, at a predetermined delay time following a significant cardiac event, or according to a predetermined schedule.

Implantable cardiac stimulating devices such as pacemakers, cardioverter-defibrillators, and devices with the combined capabilities of pacemakers and cardioverter-defibrillators are well known. A variety of devices are presently available that apply electrical pulses to a patient's heart in order to maintain a healthy heart rhythm. Some implantable cardiac devices simply apply pacing pulses to the patient's heart at regular predetermined intervals. Other implantable cardiac stimulating devices—known as rate-responsive pacemakers—are capable of applying pacing pulses at a rate commensurate with the patient's activity level. A typical rate-responsive pacemaker contains a piezoelectric activity sensor to monitor the patient's activity level. When the patient is more active, the pacemaker can increase the rate at which pacing pulses are applied to the heart, thereby increasing the patient's cardiac output as needed.

Implantable cardiac stimulating devices contain sensing circuitry for monitoring the patient's internal heartbeat signals. These internal heartbeat signals are commonly referred to as the intracardiac electrogram ("IEGM"). Cardiac stimulating devices monitor the IEGM to determine precisely when pacing pulses should be applied. For example, some implantable cardiac stimulating devices—known as demand pacemakers—apply electrical pacing pulses to the heart only in the event that the patient's heart fails to beat properly on its own. By applying pacing pulses only when needed, it is possible to avoid competition between the pulses applied by the device and the patient's intrinsic cardiac rhythm.

Further, the IEGM can be monitored to determine when the patient is experiencing a heart arrhythmia. If an arrhythmia is detected, the implantable cardiac stimulating device can attempt to return the heart to its normal rhythm. For example, some cardiac devices can determine whether the patient is suffering from an episode of tachycardia (a condition in which the heart beats too quickly) or a fibrillation event (a condition in which the heart quivers chaotically). When a tachycardia or fibrillation event is detected, a burst of weak electrical pulses or a cardioversion or defibrillation shock can be applied to the heart to terminate the arrythmia.

Cardiac stimulating devices process the IEGM to determine what type of electrical pulses should be applied to the patient's heart. Other cardiac devices, known as cardiac monitoring devices, are used solely to monitor the patient's cardiac condition. Cardiac monitoring devices are similar to cardiac stimulating devices, but do not contain pulse generating circuitry.

Both cardiac stimulating devices and cardiac monitoring devices process the IEGM to identify various cardiac events. For example, an implantable cardiac device with atrial sensing circuitry can detect P-waves, which accompany atrial contractions. Ventricular sensing circuitry can be used to detect R-waves, which accompany the contraction of the patient's ventricles.

Further, both cardiac stimulating devices and cardiac monitoring devices may contain various physiologic sensors in addition to the sensing circuitry. Typical sensors include sensors for monitoring the patient's activity level, blood oxygen level, blood pressure, blood flow rate, cardiac wall motion, temperature, and respiration rate. Cardiac sensors such as these generate data that can be stored by an implantable cardiac stimulating or monitoring device, and which aid implantable cardiac stimulating devices in determining the appropriate electrical pulses to apply to the heart.

Implantable cardiac stimulating devices have a variety of optional features, so that a physician can tailor the functions of a cardiac stimulating device to accommodate the needs of a particular patient. In this way, certain features, such as antitachycardia therapy, may be enabled for some patients, but not for others.

Programmable settings must be adjusted for the device to function optimally. For example, the physician may need to adjust the voltage at which pacing pulses are provided to the patient's heart. And the physician may wish to select the atrial and ventricular amplitude thresholds that are used to confirm when P-waves and R-waves have been detected. Numerous other programmable settings are also typically adjusted by the physician.

A physician adjusts the programmable settings of the implantable cardiac device using an external controller called a "programmer," which can communicate telemetrically with the device. The task of adjusting the programmable settings can be fairly complex and often involves making various trade-offs. For example, input settings, such as the threshold amplitudes for detecting P-waves and R-waves must not be set too low, because IEGM signals that do not correspond to P-waves and R-waves would be erroneously detected. But if the thresholds are set too high, true P-waves and R-waves will be missed.

Settings related to the output of the device, such as the pacing pulse voltage, must also be set properly. If the pulse voltage is too high, then battery power will be wasted and the patient may experience local pectoral muscle stimulation. If the pulse voltage is too low, then the heart will not be stimulated sufficiently to induce the desired response.

Physicians can evaluate the effects of adjusting the various programmable settings using a number of techniques. One approach is to monitor the patient's EKG. The EKG will often reveal whether the device is programmed properly. For example, it may be possible to observe undersensing or oversensing by the device, which generally indicates that the sensitivity of the device is not set correctly. It may also be apparent from the EKG whether the pacing or antiarrhythmia pulses of a cardiac stimulating device are having their desired effect.

However, if the physician desires to monitor the operation of the device at some time other than during a patient visit, the patient must be outfitted with a portable EKG machine (known as a Holter monitor), which is cumbersome and inconvenient for the patient. Further, the EKG may not reveal as much information as is needed by the physician. And the EKG reveals nothing about the signals being measured by the various sensors (such as an activity sensor) in the implantable cardiac device.

The physician may therefore wish to examine the patient's IEGM, because it is the IEGM that is directly monitored by the processing circuitry of the implantable cardiac device. One way to analyze the patient's IEGM is for the physician to direct the implantable cardiac device to telemetrically transmit the IEGM to a programmer, which can then be used to display the IEGM in real time. However, this approach requires the patient to make an office visit, which may be inconvenient. Further, because the data is presented in real time, unless the programmer is used to print out or otherwise store the data, the data will be lost.

It has also been observed that implantable cardiac stimulating devices sometimes function properly during the day, but not at night, when the patient is both asleep and in a supine position for a prolonged period of time. In order to determine the cause of this type of problem, the IEGM must be measured at night when the patient is asleep. However, it is generally not practicable for the physician to analyze the IEGM at night. A similar situation occurs when the patient is using cardioactive drugs. Because these drugs are often taken outside of normal office hours, it is difficult for a physician to analyze the effect of such drugs on the IEGM in real time.

Implantable cardiac devices are available that automatically store some IEGM and other cardiac data for later review by a physician upon the detection of a significant cardiac event such as the confirmation of arrhythmia or the commencement of a predetermined type of therapy (e.g., antitachycardia therapy). However, if the settings of an implantable cardiac device are not adjusted properly, the patient may experience discomfort even if the implantable cardiac device fails to classify a cardiac event as being significant enough to warrant storing the IEGM data.

Further, sometimes the physician would like to investigate the state of the IEGM several minutes after a detected cardiac event. For example, after a defibrillation shock is applied to the heart, there is typically a change in the patient's normal IEGM baseline. It would be desirable to be able to analyze the IEGM shortly after the defibrillation shock to ascertain whether the patient's IEGM has returned to its normal baseline.

As described in commonly-assigned U.S. Pat. No. 5,518,001 when a patient is experiencing discomfort, the patient may use a magnet or other triggering device to direct a implantable cardiac device to store a portion of the patient's IEGM in the memory of the device. Later, a physician can retrieve and analyze the stored IEGM data to attempt to ascertain the cause of the patient's discomfort. However, the success of this approach relies on the patient's ability to reliably trigger the implantable cardiac device at the desired time. It is therefore unsuitable to rely on this approach in situations in which the patient may forget to trigger the device or in situations where the patient is asleep.

What is needed therefore, is an improved method and apparatus that allows a physician to direct the patient's implantable cardiac device to store IEGM and other cardiac data based on a predetermined schedule. It would also be desirable if the physician could direct the implantable cardiac device to store the IEGM and other cardiac data on demand. In addition, it would be desirable if the data could be stored a predetermined period of time after a significant cardiac event is detected.

SUMMARY OF THE INVENTION

In accordance with the principles of the present invention, methods and apparatus are provided for storing an IEGM segment, cardiac sensor data, other cardiac data, and annotations (collectively called a "cardiac data record") in an implantable cardiac device memory. Cardiac data records may be stored on demand, based on a predetermined schedule, or after a predetermined delay interval following the detection of a significant cardiac event. Preferably, the memory is arranged in a number of "archive cells," each of which is suitable for storing a single cardiac data record.

If desired, the physician can compile an archive of various IEGM segments and other data for later review by storing the cardiac data records on demand, e.g., during selected office visits. The physician can retrieve the various archived data records to compare stored IEGM segments and other data to, e.g., a real time IEGM, etc. The stored data records therefore aid the physician in analyzing the patient's condition and in determining whether the implantable cardiac device is operating properly. If the physician wishes to store cardiac data records at a selected delay period after the detection of a predetermined cardiac event, the physician selects the type of events that will trigger record storage—e.g., arrhythmia detection etc. The physician also chooses the desired length of the delay period. Once the implantable cardiac device detects the predetermined cardiac event, the delay period begins. At the expiration of the delay period, the implantable cardiac device stores a cardiac data record containing the IEGM signal. This mode of operation is particularly useful if the physician wishes to determine how long it takes for the patient's IEGM to return to its normal baseline, e.g., following a significant event such as a detected tachycardia episode that has been terminated by a cardioversion shock.

If the physician is interested in sampling the patient's IEGM at night, or at a particular time following the patient's use of a cardioactive drug, then the physician can program the implantable cardiac device to store a cardiac data record at a suitable time, i.e., according to a schedule. At the designated time, the implantable cardiac device stores the cardiac data records for later retrieval and review by the physician.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
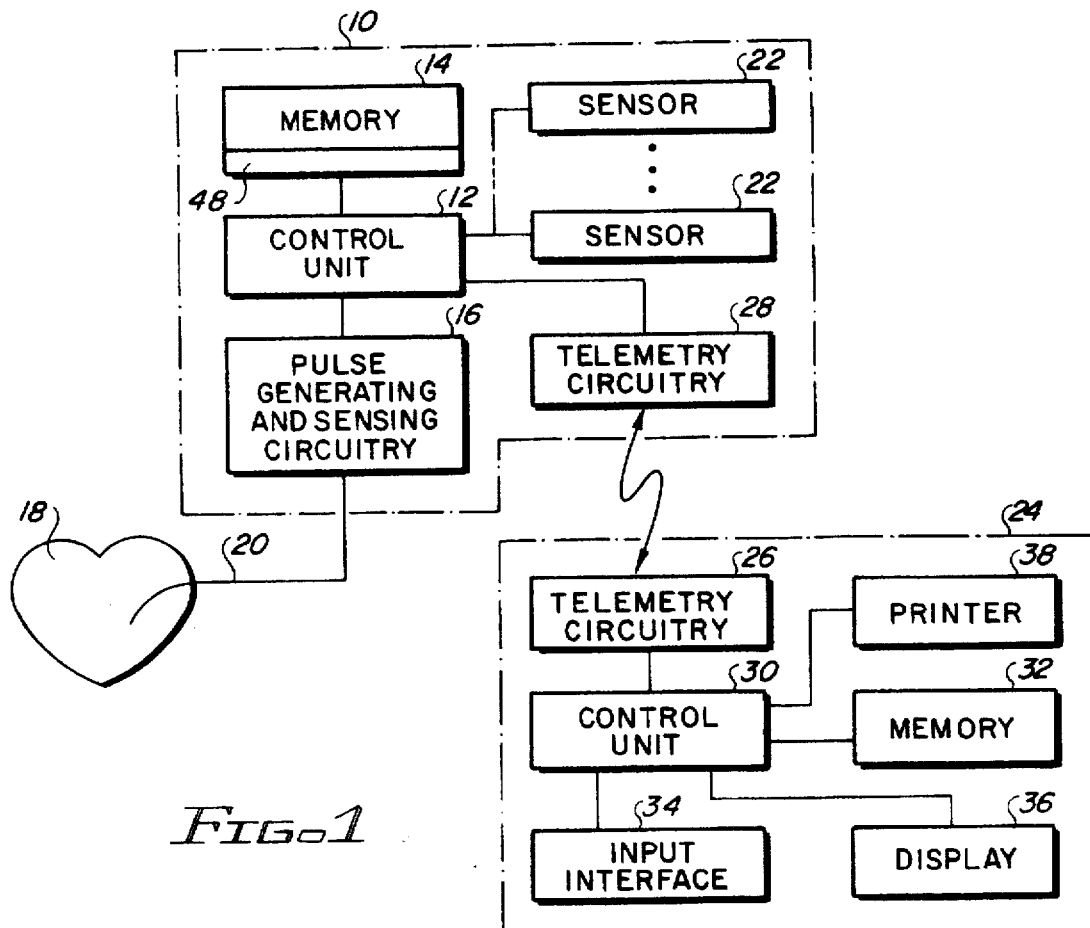
FIG. 1 is a simplified schematic block diagram of an illustrative programmable implantable cardiac device and programmer.

An illustrative implantable cardiac device 10 constructed in accordance with the present invention is shown in FIG. 1. The implantable cardiac device 10 is controlled by a control unit 12, which is preferably microprocessor-based. The control unit executes instructions contained in a memory 14 (e.g., a 128K static random-access memory). The cardiac device 10 applies electrical pulses from the pulse generating and sensing circuitry 16 to a patient's heart 18 via a lead 20. The pulse generating and sensing circuitry 16 is also used to measure the patient's IEGM. The implantable cardiac device 10 illustrated in FIG. 1 is preferably capable of stimulating the heart with the pulse generating and sensing circuitry 16, but the invention is equally applicable to implantable cardiac devices that provide solely monitoring functions. Cardiac monitoring devices contain sensing circuitry in place of pulse generating and sensing circuitry 16.

The implantable cardiac device 10 preferably contains one or more sensors 22, such as an activity sensor, blood oxygen sensor, blood pressure sensor, blood flow rate sensor, cardiac wall motion sensor, temperature sensor, and respiration rate sensor. The sensors 22 provide cardiac data that is used by the control unit 12 in conjunction with the IEGM data to determine how to control the implantable cardiac device 10.

In order to adjust the programmable settings of the implantable cardiac device 10, a physician uses a programmer 24. The programmer 24 contains telemetry circuitry 26 for communicating telemetrically with telemetry circuitry 28 of the implantable cardiac device 10. The operation of the programmer 24 is controlled by a control unit 30, which is preferably microprocessor-based. The control unit 30 executes instructions stored in a memory 32. The physician enters commands into the programmer 24 via an input interface 34, which may be any suitable input interface such as a keyboard, trackball, touchpad, pen-based computer screen, joystick, etc. Cardiac data such as IEGM data telemetered from the implantable cardiac device 10 can be displayed on a display 36, which may be any suitable display such as a liquid crystal display, cathode ray tube, plasma display, or other conventional monitor. A hard copy of the data shown on the display 36 may be printed out using a conventional printer 38.

In accordance with the present invention, the physician can direct the implantable cardiac device 10 to store IEGM and other cardiac data in three separate ways. First, if the physician wants to create a semipermanent record of the IEGM and cardiac sensor data currently being measured by the implantable cardiac device 10, the physician can direct the cardiac stimulating device 10 to store the data "on demand." A number of such "cardiac data records" can be stored for later retrieval and analysis by the physician. Storing these data records aids the physician in assessing the patient's condition and in determining whether or not the implantable cardiac device 10 is operating properly.

A second method for storing cardiac data records is for the physician to select a delay period to follow a predetermined cardiac event (such as a confirmed arrhythmia episode). Once the implantable cardiac device 10 detects the predetermined cardiac event, the delay period begins. At the expiration of the delay period, the implantable cardiac device 10 stores a cardiac data record. This feature is useful if the physician wishes to determine how long it takes for the patient's IEGM to return to its normal baseline, e.g., following a significant event such as a detected tachycardia episode that has been terminated by a cardioversion shock.

Third, the physician can program the implantable cardiac device 10 to store cardiac data records according to a predetermined schedule. For example, if the physician is interested in sampling the patient's IEGM at night, or at a particular time following the patient's use of a cardioactive drug, then the physician can program the implantable cardiac device 10 to store a cardiac data record at a suitable time. At the designated time, the implantable cardiac device 10 stores the cardiac data records for later retrieval and review by the physician.

Figure 2:
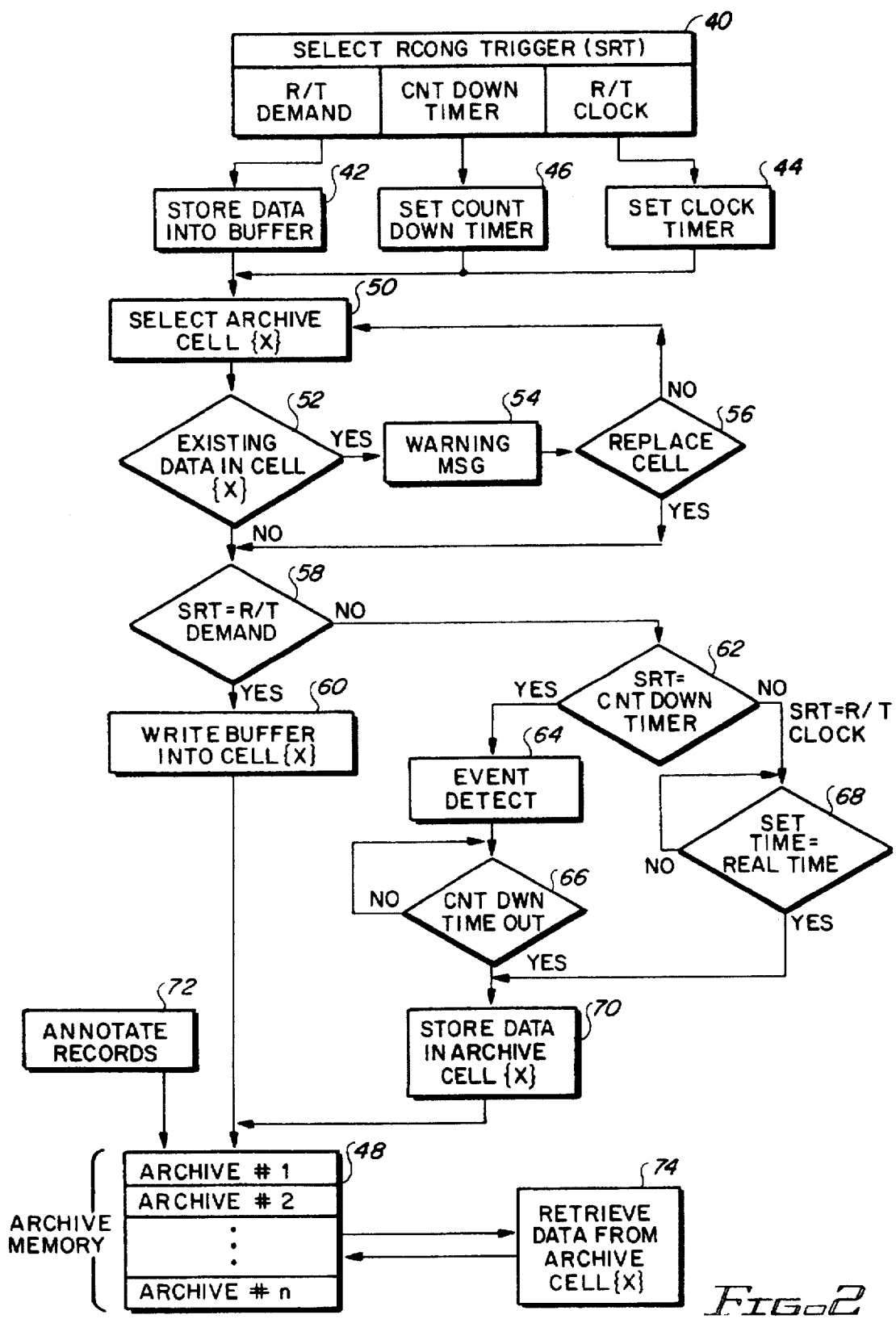
FIG. 2 is an illustrative flow chart showing the various steps performed in order to store cardiac data records in accordance with the present invention.

The implantable cardiac device 10 is preferably provided with instructions in the memory 14 that allow the implantable cardiac device 10 to provide each of these features. A flow chart illustrating some aspects of the present invention is shown in FIG. 2. At a step 40 the physician determines whether it is desired to store a patient's cardiac data record in the memory 14 (FIG. 1) (1) immediately (i.e., on demand), (2) at a designated delay time following a predetermined cardiac event, or (3) according to a predetermined schedule.

If the physician directs the implantable cardiac device to store a cardiac data record immediately, then the IEGM segment and other data that make up the data record are preferably stored into a memory buffer at a step 42. The memory buffer is preferably a dedicated portion of the memory 14 (FIG. 1). If the physician decided at the step 40 to store cardiac data records according to a schedule, then the physician preferably programs the desired schedule into the implantable cardiac device 10 (FIG. 1) at a step 44, using the programmer 24 (FIG. 1). If the physician decided at the step 40 that cardiac data records should be stored at a certain delay time following a confirmed cardiac event, the physician programs the implantable cardiac device 10 (FIG. 1) accordingly, using the programmer 24 (FIG. 1) at a step 46.

Preferably, the IEGM, cardiac data, and accompanying annotations (which may be provided by a physician) that make up the cardiac data record to be stored by the implantable cardiac device 10 (FIG. 1) are stored in a memory region 48 (FIGS. 1 and 2) of the memory 14 (FIG. 1). The memory region 48 is preferably large enough to accommodate a number of cardiac data records. Each cardiac data record may be stored in a separate portion of the memory region 48, called an "archive cell." Preferably, the memory region 48 has at least eight archive cells, so that up to eight separate cardiac data records can be stored.

At a step 50, the physician can select which of the archive cells the next record should be stored in. If the physician does not select a new archive cell, the implantable cardiac device 10 will preferably save the next record into the least recently updated cell. At a test 52, it is determined whether or not there is existing data in the selected cell. If there is existing data, a warning message can be generated at a step 54. The physician can decide whether to overwrite existing data at a test 56.

At a test 58, it is determined whether or not a cardiac data record was stored into the buffer at the step 42 (i.e., whether the record was created on demand). If the record was created on demand, the record is transferred from the buffer into the appropriate archive cell at a step 60.

At a test 62, it is determined whether the record is to be created following a programmed delay time period after a detected cardiac event. If it is, then after the preselected cardiac event is confirmed at a step 64, control loops continuously at a test 66 until a countdown timer exceeds the appropriate timing (delay. If the cardiac data record is created according to a schedule, then control loops continuously at a test 68 until a real time clock reaches the scheduled time to create the data record. The countdown timer and real time clock features are preferably provided by circuitry contained within the control unit 10 (FIG. 1).

After the countdown timer reaches the delay time at a test 66 or the real time clock reaches the designated time, the control unit 12 (FIG. 1) stores the cardiac data record in the appropriate archive cell at a step 70. At the same time that the cardiac data record is stored in the memory region 48, date and time information is preferably appended to the cardiac data record. When the patient returns for an office visit, the physician may also annotate the cardiac data records at a step 72, if desired, using the programmer 24 (FIG. 1). At a step 74, the physician can also use the programmer 24 (FIG. 1) to retrieve the cardiac data records stored in the archive cells to compare the stored data to real time signals and to analyze the performance of the implantable cardiac device 10 (FIG. 1) and the condition of the patient.

Each cardiac data record preferably contains a recorded IEGM segment having at least four intrinsic or paced cardiac events, date and time information, data from any sensors in operation (such as an activity sensor), and optional annotations from the physician. Preferably, the cardiac data records also contain event markers (such as the letter "R" indicating detection of an R-wave) that are generated by the implantable cardiac device 10 (FIG. 1) during the recording of the IEGM.

Figure 3:
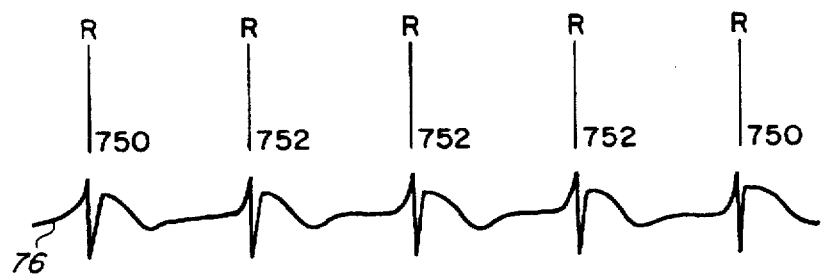
FIG. 3 is an illustrative print out of a stored IEGM segment and corresponding physician annotation.

An illustrative display format for the cardiac data records on the display 36 (FIG. 1) of the programmer 24 (FIG. 1) is shown in FIG. 3. An IEGM segment 76 containing five confirmed R-waves, each corresponding to a ventricular contraction, is shown. An indicator line 78 is preferably placed above each detected R-wave, along with the label "R" and the time (in ms) elapsed between successive beats.

The record of FIG. 3 has been annotated "NSR @ 80 bpm" to indicate that the IEGM corresponds to a normal sinus rhythm of 80 beats per minute. Further, the status of various programmable options (such as the lead configuration and input sensitivity) of the implantable cardiac device 10 (FIG. 1) is shown. The data relating to the status of the programmable options at the time the IEGM segment was acquired is preferably made a part of the cardiac data record by the control unit 12 (FIG. 1) during the process of storing each cardiac data record in the memory region 48 (FIGS. 1 and 2).

Referring again to FIG. 1, some of the processing necessary to provide the information to be displayed on the display 36 is performed by the control unit 12 of the implantable cardiac device 10 and some is performed by the control unit 30 of the programmer 24. Whether it is preferable for the control unit 12 or the control unit 30 to be used to process the cardiac data depends, in part, on the relative ease of implementation of the desired processing function in each unit. For example, the time elapsed between successive detected R-waves is preferably placed on the display 36 as an aid to the physician. But it may not be desirable for the implantable cardiac device 10 to calculate the time elapsed between beats. Rather, it may be preferable for the implantable cardiac device 10 to be configured simply to store event markers along with the time each event is detected. When this data is retrieved from the cardiac data record, the control unit 30 of the programmer 24 can be used to calculate the time elapsed between successive beats. Alternatively, if the implantable cardiac device 10 is configured so that the time elapsed between successive beats is stored in each cardiac data record, then that information need not be generated by the control unit 30.

Thus, it is seen that methods and apparatus are provided for storing intracardiac electrogram (IEGM) segments and other cardiac data in an implantable cardiac device. When a physician wishes to create a cardiac data record containing the IEGM and cardiac data, the physician directs the cardiac device to store the data on demand. A number of cardiac data records can be stored. Data records may also be stored after a delay period following a predetermined cardiac event. When the implantable cardiac device detects the predetermined cardiac event, the delay period begins. At the expiration of the delay period, the implantable cardiac device stores a cardiac data record. Further, cardiac data records can be stored according to a predetermined schedule.

One skilled in the art will appreciate that the present invention can be practiced by other than the described embodiments, which are presented for the purposes of illustration and not of limitation, and the present invention is limited only by the claims that follow.

What is claimed is:

1. An implantable cardiac device for measuring a plurality of intracardiac electrogram segments, generating a plurality of user selectable cardiac data records each of which contains an intracardiac electrogram segment, and receiving telemetric commands from a programmer, the implantable cardiac device comprising:

a memory containing a plurality of archive cells;

a control unit;

sensing circuitry, connected to the control unit, for measuring the plurality of intracardiac electrogram segments; and receiving circuitry for receiving a plurality of storage commands from the programmer, wherein:

the control unit stores user selectable cardiac data records, each of which contains a respective one of the plurality of intracardiac electrogram segments in respective ones of the plurality of archive cells in response to respective storage commands;

the control unit further comprising selecting circuitry for providing user selection of a specific one of the archive cells into which a given one of the cardiac data records is stored;

a predetermined cardiac event detector for initiating a delay time countdown following detection of the predetermined cardiac event; wherein:

the memory contains a first additional archive cell;

when the delay time countdown is finished the sensing circuitry measures a first additional intracardiac electrogram segment; and the control unit stores a first additional cardiac data record containing the first additional intracardiac electrogram segment in the first additional archive cell.

2. The implantable cardiac device defined in claim 1, wherein the control unit further comprises circuitry for generating a warning message when the specific archive cell contains data prior to storing the given one of the cardiac data records in the specific archive cell.

3. The implantable cardiac device defined in claim 1, wherein the control unit further comprises circuitry for including time and date data in at least one of the cardiac data records.

4. The implantable cardiac device defined in claim 1, wherein the control unit further comprises circuitry for including event markers in at least one of the cardiac data records.

5. The implantable cardiac device defined in claim 1, further comprising a cardiac data sensor coupled to the control unit, wherein the control unit includes data from the cardiac data sensor in at least one of the cardiac data records.

6. The implantable cardiac device defined in claim 1, wherein the control unit further comprises:

schedule circuitry for establishing a scheduled time at which a second additional cardiac data record is to be stored; and detection circuitry for detecting when the scheduled time has been reached, the memory containing a second additional archive cell and the sensing circuitry measuring a second additional intracardiac electrogram segment, such that when the detection circuitry determines that the scheduled time has been reached the control unit stores a second additional cardiac data record containing the second additional intracardiac electrogram segment in the second additional archive cell.

7. An implantable cardiac device for measuring intracardiac electrogram segments, generating user selectable cardiac data records each of which contains an intracardiac electrogram segments, and receiving telemetric commands from a programmer, the implantable cardiac device comprising:

a memory containing an archive cell;

control unit;

sensing circuitry connected to the control unit for measuring the intracardiac electrogram segments; and receiving circuitry for receiving a storage command from the programmer, wherein:

the sensing circuitry measures an intracardiac electrogram segment;

the control unit stores a cardiac data record containing the measured intracardiac electrogram segment in the archive cell in response to the storage command; and the control unit further comprises circuitry for appending physician user-inputted annotations onto the cardiac data record.

8. A method of creating an archive of cardiac data in an implantable cardiac device that contains a memory and sensing circuitry for measuring a plurality of intracardiac electrogram segments, and which receives telemetric commands from a programmer, the method comprising the steps of:

providing a plurality of archive cells within the memory;

measuring a plurality of intracardiac electrogram segments;

receiving a plurality of storage commands from the programmer; and storing a plurality of cardiac data records each of which contains a respective one of the intracardiac electrogram segments in respective archive cells in response to respective storage commands; and providing for user selection of a specific one of the archive cells into which a given one of the cardiac data records is to be stored.

9. The method defined in claim 8, further comprising the step of generating a warning message when the specific archive cell contains data prior to storing the given one of the cardiac data records in the specific archive cell.

10. The method defined in claim 8, wherein the step of storing the cardiac data records further comprises the step of including time and date data in at least one of the cardiac data records.

11. The method defined in claim 8, wherein the step of storing the cardiac data records further comprises the step of including event markers in at least one of the cardiac data records.

12. The method defined in claim 8, wherein the step of storing the cardiac data record further comprises the step of including data from a cardiac data sensor in the cardiac data record.

13. The method defined in claim 8 further comprising the steps of:

providing a first additional archive cell within the memory;

measuring a first additional intracardiac electrogram segment;

detecting when a predetermined cardiac event has occurred;

initiating a delay time countdown following detection of the predetermined cardiac event; and storing a first additional cardiac data record containing the first additional intracardiac electrogram segment in the first additional archive cell when the delay time countdown is finished.

14. The method defined in claim 13, further comprising the steps of:

providing a second additional archive cell within the memory;

measuring a second additional intracardiac electrogram segment;

establishing a scheduled time at which a second additional cardiac data record containing the second additional intracardiac electrogram segment is to be stored; and storing the second additional cardiac data record in the second additional archive cell when the scheduled time is reached.

15. A method of creating an archive of cardiac data in an implantable cardiac device that contains a memory and sensing circuitry for measuring intracardiac electrogram segments, and which receives telemetric commands from a programmer, the method comprising the steps of:

providing an archive cell within the memory;

measuring an intracardiac electrogram segment;

receiving a storage command from the programmer; and storing a cardiac data record containing the measured intracardiac electrogram segment in the archive cell in response to the storage command, wherein the step of storing the cardiac data record further comprises the step of including physician annotations in the cardiac data record.

16. An implantable cardiac device for measuring intracardiac electrogram segments, generating cardiac data records each of which contains one of the intracardiac electrogram segments, and receiving telemetric commands from a programmer, the implantable cardiac device comprising:

a memory containing a first archive cell;

a control unit;

sensing circuitry connected to the control unit for measuring the intracardiac electrogram segments;

schedule circuitry for establishing a scheduled time of day at which a first cardiac data record is to be stored; and detection circuitry for detecting when the scheduled time is reached, such that when the scheduled time of day is reached the sensing circuitry measures a first intracardiac electrogram segment and the control unit stores the first cardiac data record containing the first intracardiac electrogram segment in the first archive cell.

17. The implantable cardiac device defined in claim 16, wherein:

the memory contains additional archive cells;

the schedule circuitry establishes additional scheduled times at which additional cardiac data records are to be stored;

when the scheduled times have been reached the sensing circuitry measures additional ones of the intracardiac electrogram segments;

each of the additional cardiac data records contains a respective one of the additional intracardiac electrogram segments; and when the scheduled times have been reached the control unit stores each of the additional cardiac data records in a respective one of the additional archive cells.

18. The implantable cardiac device defined in claim 16, wherein the control unit further comprises circuitry for including time and date data in the first cardiac data record.

19. The implantable cardiac device defined in claim 16, wherein the control unit further comprises circuitry for including event markers in the first cardiac data record.

20. The implantable cardiac device defined in claim 16, wherein the control unit further comprises circuitry for appending physician annotations onto the first cardiac data record.

21. The implantable cardiac device defined in claim 16, further comprising a cardiac data sensor coupled to the control unit, wherein the control unit includes data from the cardiac data sensor in the first cardiac data record.

22. The implantable cardiac device defined in claim 16, further comprising:

receiving circuitry for receiving a storage command from the programmer, wherein:

the memory contains a second archive cell;

the sensing circuitry measures a second intracardiac electrogram segment; and the control unit stores a second cardiac data record containing the second intracardiac electrogram segment in the second archive cell in response to the storage command.

23. The implantable cardiac device defined in claim 22, wherein the control unit stores a given one of the cardiac data records into a specific selected one of the archive cells.

24. The implantable cardiac device defined in claim 23, wherein the control unit generates a warning message when the specific archive cell contains data prior to storing the given one of the cardiac data records in the specific archive cell.

25. The implantable cardiac device defined in claim 24, further comprising:

a predetermined cardiac event detector for detecting when a predetermined cardiac event has occurred;

a delay time countdown initiator for initiating a delay time countdown following detection of the predetermined cardiac event; wherein:

the memory contains a third archive cell; and the sensing circuitry measures a third intracardiac electrogram segment, such that when the delay time countdown is finished the control unit stores a third cardiac data record containing the third intracardiac electrogram segment in the third archive cell.

26. A method of creating an archive of cardiac data in an implantable cardiac device that contains a memory and sensing circuitry for measuring intracardiac electrogram segments, and which receives telemetric commands from a programmer, the method comprising the steps of:

providing a first archive cell within the memory;

measuring a first intracardiac electrogram segment;

establishing a scheduled time of day at which a first cardiac data record containing the first intracardiac electrogram segment is to be stored; and storing the first cardiac data record in the first archive cell when the scheduled time of day has been reached.

27. The method defined in claim 26, further comprising the steps of:

providing additional archive cells within the memory;

measuring additional ones of the intracardiac electrogram segments;

establishing additional scheduled times at which additional cardiac data records each containing a respective one of the additional intracardiac electrogram segments are to be stored; and storing the additional cardiac data records in respective ones of the additional archive cells as each of the scheduled times is reached.

28. The method defined in claim 26, wherein the step of creating the first cardiac data record further comprises the step of including time and date data in the first cardiac data record.

29. The method defined in claim 26, wherein the step of creating the first cardiac data record further comprises the step of including event markers in the first cardiac data record.

30. The method defined in claim 26, wherein the step of creating the first cardiac data record further comprises the step of including physician annotations in the first cardiac data record.

31. The method defined in claim 26, wherein the step of creating the first cardiac data record further comprises the step of including data from a cardiac data sensor in the first cardiac data record.

32. The method defined in claim 26, further comprising the steps of:

providing a second archive cell within the memory;

measuring a second intracardiac electrogram segment;

receiving a storage command from the programmer; and storing a second cardiac data record containing the second intracardiac electrogram segment in the second archive cell in response to the storage command.

33. The method defined in claim 32, further comprising the step of selecting a specific one of the archive cells into which a given one of the cardiac data records is to be stored.

34. The method defined in claim 33, further comprising the step of generating a warning message when the specific archive cell contains data prior to storing the given one of the cardiac data records in the specific archive cell.

35. The method defined in claim 32 further comprising the steps of:

providing a third archive cell within the memory;

measuring a third intracardiac electrogram segment;

detecting when a predetermined cardiac event has occurred;

initiating a delay time countdown following detection of the predetermined cardiac event; and storing a third cardiac data record containing the third intracardiac electrogram segment in the third archive cell when the delay time countdown is finished.

* * * * *